United States Patent [19]

Janoff et al.

[11] Patent Number: 4,698,299

[45] Date of Patent: Oct. 6, 1987

[54] LIPID-DEPENDENT DIAGNOSTIC ASSAYS

[75] Inventors: Andrew S. Janoff, Yardley, Pa.; Joyce Rauch, Montreal; Colin P. S. Tilcock, Vancouver, both of Canada

[73] Assignee: The Liposome Company, Inc., Princeton, N.J.

[21] Appl. No.: 831,255

[22] Filed: Feb. 19, 1986

Related U.S. Application Data

[63] Continuation-in-part of Ser. No. 702,555, Feb. 19, 1985.

[51] Int. Cl.$^4$ ............... G01N 33/564; G01N 33/571; G01N 33/96
[52] U.S. Cl. ........................... 435/13; 435/7; 436/175; 436/506; 436/511; 436/825
[58] Field of Search .............. 436/511, 175, 825, 506; 435/13

[56] References Cited

U.S. PATENT DOCUMENTS

| | | | |
|---|---|---|---|
| 3,564,089 | 2/1971 | Kiddy | 436/511 |
| 3,600,494 | 8/1971 | Tomizawa | 436/511 |
| 4,076,797 | 2/1978 | Davis | 436/511 X |
| 4,273,867 | 6/1981 | Lin | 436/825 X |

OTHER PUBLICATIONS

Boey, M. L. et al., "Thrombosis in Systemic Lupus Erythematosus: Striking Association With the Presence of Circulating Lupus Anticoagulant," British Med. Journ., 287, pp. 1021-1023, 1983.
Margolius, A. et al., "Circulating Anticoagulants: A Study of 40 Cases and a Review of the Literature," Medicine, 40, pp. 145-202, 1961.
Lafer, E. M. et al., "Polyspecific Monoclonal Lupus Autoantibodies Reactive With Both Polynucleotides and Phospholipids", Journal Experimental Medicine, 153, pp. 897-909, 1981.
Folch, J. "Brain Cephalin, a Mixture of Phosphatides, Separation from it of Phosphatidyl Serine, Phosphatidyl Ethanolamine & a Fraction Containing an Inositol Phosphatide," J. Biol. Chem., 146, pp. 35-44, 1942.
Exner, T. et al., "Studies on Phospholipids in the Action of a Lupus Coagulation Inhibitor," Pathology, 7, pp. 319-328, 1975.
Thiagarajan, P., et al., "Monoclonal Immunoglobulin Mλ Coagulation Inhibitor With Phospholipid Specificity," J. Clin. Invest., 66, pp. 397-405, 1980.
Sparling, P. "Diagnosis and Treatment of Syphilis", New England Journal of Medicine, 284, pp. 642-653, 1971.

*Primary Examiner*—Sidney Marantz
*Attorney, Agent, or Firm*—Allen Bloom; Catherine L. Kurtz

[57] ABSTRACT

Lipid-dependent diagnostic assays are provided wherein the test sample to be assayed is pre-incubated with one or more phospholipids having a hexagonal ($H_{II}$) organization, with lipidic particles, or with bilayer-forming lysophospholipids such as monooleoylphosphatidylethanolamine (MOPE). The pre-incubation results in reduced false positives due to antiphospholipid antibodies, such as, lupus anticoagulants, which may be present in the test sample, without changing the overall character, including the normal baseline, of the assay. Surprisingly, in accordance with the invention, it has been found that only hexagonal phospholipids, lipidic particles, and bilayer-forming lysophospholipids can be used, and, in particular, lamellar (bilayer) phospholipids (other than such lysophospholipids) cannot be used. An assay for diagnosing systemic lupus erythematosus (SLE) is also provided.

14 Claims, 5 Drawing Figures

LIPID-DEPENDENT DIAGNOSTIC ASSAYS

RELATED COPENDING APPLICATIONS

This application is a continuation-in-part of copending patent application Ser. No. 702,555, filed Feb. 19, 1985.

BACKGROUND OF THE INVENTION

1. Field of the Invention

This invention relates to diagnostic assays and in particular to diagnostic assays which employ phospholipids as assay reagents.

2. Description of the Prior Art

A variety of diagnostic assays are known which include one or more phospholipids as assay reagents. For example, various blood coagulation tests, such as, complete and partial thromboplastin times, prothrombin times, and the like, employ brain and other tissue extracts which include lipids. Similarly, the VDRL (Venereal Disease Research Laboratory) test for syphilis is based on the use of an antigen solution which includes cardiolipin, cholesterol and lecithin.

As with many assay systems, the foregoing assays suffer from the problem of false positives, i.e., for certain patients, the coagulation tests give results indicative of a coagulation problem, when, in fact, the patient's clotting mechanisms are normal, or, in the case of the VDRL test, the patient appears to have syphilis, when in fact he or she is syphilis free.

Prior studies have established a correlation between these false positives and certain diseases. For example, blood samples from patients having the autoimmune disease, systemic lupus erythematosus (SLE), often have prolonged coagulation times, even though clinically, the patients do not exhibit bleeding tendencies and, indeed, in some cases, may suffer from thrombotic episodes. The blood of such patient is said to certain coagulation inhibitors," "lupus inhibitors," "circulating anticoagulants," or "lupus anticoagulants." See T. Exner, et al., "Studies on Phospholipids in the Action of a Lupus Coagulation Inhibitor," *Pathology*, Vol. 7, 1975, pages 319-328; and P. Thiagarajan, et al., "Monoclonal Immunoglobulin Mλ Coagulation Inhibitor with Phospholipid Specificity," *J. Clin. Invest.*, Vol. 66, September 1980, pages 397-405.

It is presently believed that these "inhibitors" are in fact antibodies against phospholipids which are produced by the immune system of patients suffering from SLE. See P. Thiagarajan, et al., supra. Similar anti-phospholipid antibodies have been found in the sera of patients suffering from other autoimmune diseases, such as, connective tissue diseases, Hashimoto's thyroiditis, rheumatoid arthritis, and the like. See P. F. Sparling, "Diagnosis and Treatment of Syphilis," *New England Journal of Medicine*, Vol. 284, pages 642-653 (1971). Accordingly, patients with these diseases are also likely to give false positives when subjected to lipid-dependent diagnostic assays.

Efforts have been made in the past to solve the problem of false positives in lipid-dependent assays, and, in particular, lipid-dependent coagulation assays, but with only limited success. Thus, Exner, et al., supra, reported that the effect of lupus inhibitor on the Russell viper venom coagulation test could be partially corrected by adding to the reagent mixture what Exner referred to as "partially characterized" phospholipids obtained from bovine cephalin using the Folch procedure. See J. Folch, "Brain Cephalin, A Mixture of Phosphatides. Separation from it of Phosphatidyl Serine, Phosphatidyl Etanolamine, and a Fraction Containing an Inositol Phosphatide," *J. Biol. Chem.*, Vol. 146, 1942, pages 35-41.

Exner tested three phospholipid fractions identified as phosphatidyl ethanolamine, phosphatidyl serine, and inositol phosphatide. As reported by Exner, at low concentrations, each fraction reduced somewhat the clotting times of plasma samples containing lupus inhibitor, but not to the levels observed for normal samples (see page 324 and FIGS. 2A, 2B, and 2C of Exner, et al.). At higher concentrations, the addition of these phospholipid fractions unfortunately changed both the clotting times of the inhibitor-containing samples and the clotting times of the normal samples, i.e., rather than solving the false positive problem, the addition of these phospholipids to the reagent mixture resulted in a change in the overall response, including the baseline, of the assay. Of the three phospholipid fractions tested, Exner stated that the phosphatidyl ethanolamine fraction appeared to give the best corrective effect.

In addition to the Exner work, Thiagarajan, et al., supra, studied the effects on coagulation assays of purified IgMλ paraprotein obtained from a patient whose response to lipid-dependent coagulation tests indicated the presence in the patient's blood of a lupus-type anticoagulant. The purified paraprotein, when added to normal plasma, was found to reproduce the abnormal coagulation time observed with the patient's plasma. Studies using the paraprotein indicated that it reacted with phosphatidylserine and, to a lesser extent, with phosphatidylinositol and phosphatidic acid, but that it did not react with phosphatidylcholine or phosphatidylethanolamine.

A comparison of the results reported by Thiagarajan with those reported by Exner highlights the confusing state of the prior art. Whereas Thiagarajan, et al., found that their lupus anticoagulant would not react with phosphatidylethanolamine, Exner, et al., found just the opposite. Moreover, in Exner's hands, phosphatidylethanolamine distorted the basic character of the assay as evidenced by the fact that the presence of 0.05% phosphatidylethanolamine in the reagent mixture resulted in an over 40% increase in the clotting time of normal plasma and only a 30% decrease in the clotting time of a mixture of 90% normal plasma and 10% patient plasma (see FIG. 2A of Exner, et al.). It is against this background that the present invention was made.

SUMMARY OF THE INVENTION

In view of the foregoing state of the art, it is an object of the present invention to provide improved lipid-dependent diagnostic assays which are less likely to exhibit false positives when used to test blood samples which include anti-phospholipid antibodies. It is a further object of the invention to provide such improved assays without changing the original character of the assay and, in particular, without changing the original baseline of the assay.

It is another object of the invention to provide improved lipid-dependent assays of the foregoing types which are less likely to exhibit false positives when used to test blood samples which include a lupus anticoagulant or inhibitor.

It is an additional object of the invention to provide coagulation assays and syphilis assays which have been improved in the foregoing ways.

It is a further object of the invention to provide assays useful in determining whether or not a patient has systemic lupus erythematosus.

To achieve the foregoing and other objects, the invention in accordance with certain of its aspects provides a process for reducing the effect of antiphospholipid antibodies on lipid-dependent diagnostic assays comprising the steps of combining the sample to be assayed with one or more lipids having a hexagonal ($H_{II}$) organization, (hereinafter referred to as "hex II lipids, "hexagonal lipids", or "hex II phase lipids"), incubating the sample and the one or more hex II phase lipids for a predetermined period of time, and then performing the lipid-dependent assay following the assay's standard protocol. Alternatively, rather than using lipids having a hexagonal ($H_{II}$) organization, lipidic particles or bilayer-forming lysophospholipids such as monooleoylphosphatidylethanolamine (MOPE) can be incubated with the sample.

As explained in detail in connection with the description of the preferred embodiments, in accordance with the invention, it has been discovered that by following the foregoing pre-incubation procedure, the level of false positives of lipid-dependent diagnostic assays can be reduced without changing the character, including the normal baseline, of the assay. Significantly, if lipids having a lamellar organization, other than bilayer-forming lysophospholipids, are used instead of hex II lipids or lipidic particles, the effects of anti-phospholipid antibodies on lipid-dependent assays are not diminished. It is believed that the confused state of the prior art is a result of the fact that the art had not in any way recognized that it is a lipid's organizational state which determines whether or not it will be capable of decreasing diagnostic false positives in the presence of anti-phospholipid antibodies.

In addition to the foregoing aspects, the invention also provides a diagnostic assay for lupus. In accordance with this aspect, first and second samples of a patient's plasma are subjected to a lipid-dependent assay, the second sample having been pre-incubated with one or more hex phase lipids, lipidic particles, or bilayer-forming lysophospholipids. The presence of lupus, or, more particularly, the presence of a lupus anticoagulant in the patient's plasma, is indicated by the combination of a positive result for the assay performed on the first sample and a normal result for the assay performed on the second sample. Of course, because this combination can occur for other diseases which lead to the production of antiphospholipid antibodies (see discussion above), in making a final determination of whether or not lupus is present, the results of the assay of the present invention are preferably used in combination with other information, e.g., the patient's presenting symptoms and the results of other assays. Among the lipid-dependent assays which can be used for this aspect of the invention are coagulation time assays, e.g., a partial thromboplastin time (PTT) assay, and cardiolipin-dependent syphilis tests, e.g., the VDRL test.

$$\% \text{ inhibition} = \frac{PTT \text{ (maximum)} - PTT \text{ (sample)}}{PTT \text{ (maximum)} - PTT \text{ (minimum)}} \times 100\%$$

Figure 3:
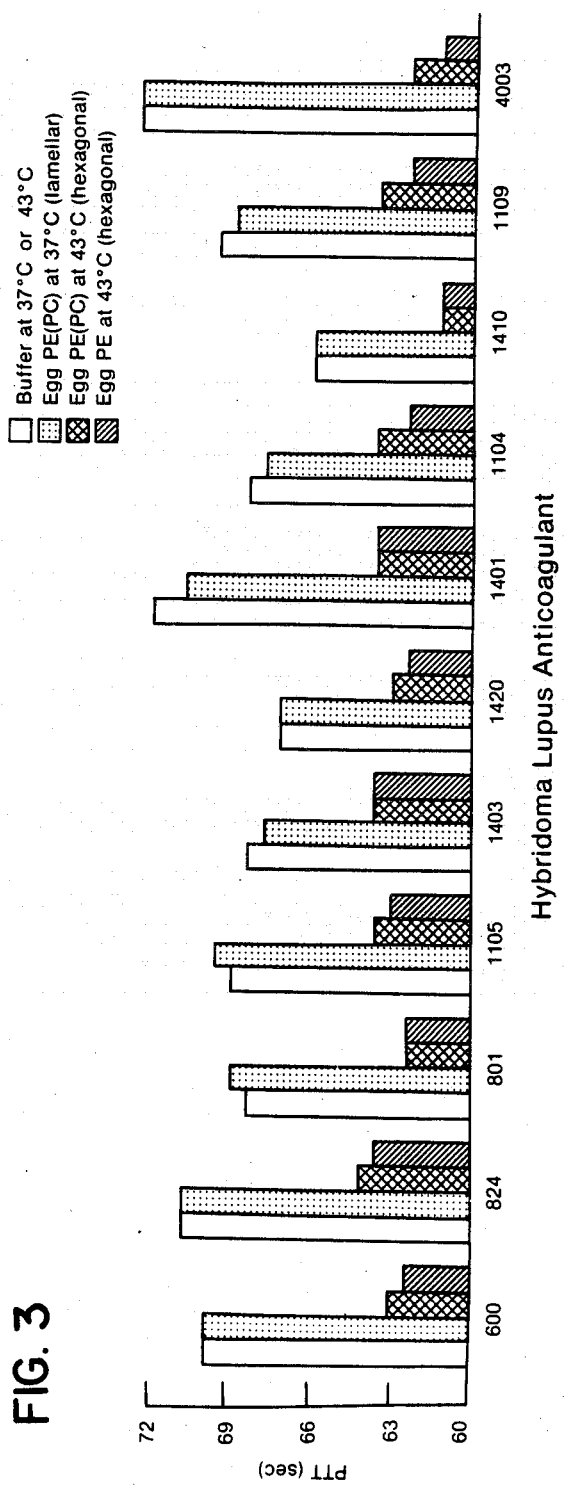

FIG. 3 shows the effect of pre-incubation of hybridoma lupus anticoagulants with buffer and egg PE(PC) at 37° C. and 43° C. and egg PE at 43° C. Each bar represents the mean PTT of duplicate samples. The mean PTT of the negative controls (GM 4672 IgG and 1500 IgM) of these experiments was 1.00 min.±0.02. The amounts of egg PE(PC) and egg PE added to the hybridoma antibodies were 89.8 and 114.4 nanomoles phosphorus, respectively.

Figure 4:
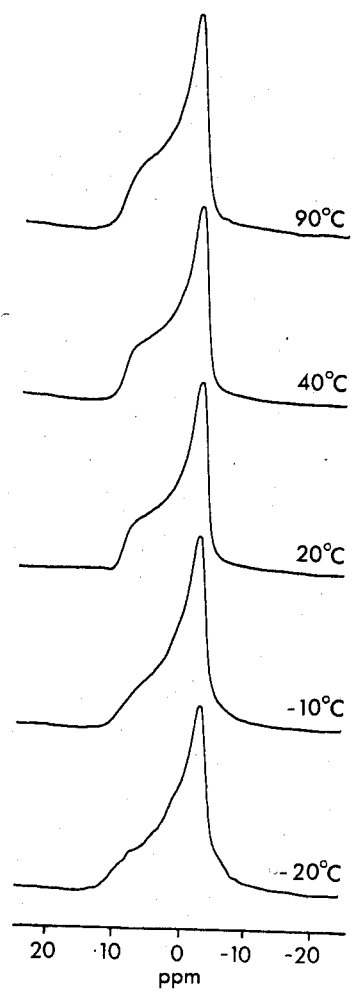

FIG. 4 shows $^{31}P$ NMR spectra of MOPE between −20° C. and 90° C. As shown by the tracings, MOPE displays spectra consistent with a lamellar configuration.

DESCRIPTION OF THE PREFERRED EMBODIMENTS

As described above, in accordance with one of its aspects, the present invention relates to a method for decreasing false positives in lipid-dependent assays by pre-incubating test samples with hex II lipids, lipidic particles, or bilayer-forming lysophospholipids.

As has been established by various techniques, including X-ray diffraction, freeze-fracture, and $^{31}P$ NMR studies, lipids can exist in a variety of macromolecular organizations. See, for example, P. Cullis, et al., "Structural Properties of Lipids and Their Functional Roles in Biological Membranes," in *Membrane Fluidity in Biology*, Vol. 1, Academic Press, 1983, Chapter 2, pages 39–81. Which organization exists in a particular lipid solution depends on various factors, including, the lipid or lipids involved, the temperature of the solution, the pH of the solution, the solution's ionic strength, the concentration of divalent cations, in particular, $Ca^{2+}$, in the solution, and, in the case of unstable configurations, the length of time the lipids have been in solution.

Figure 1:
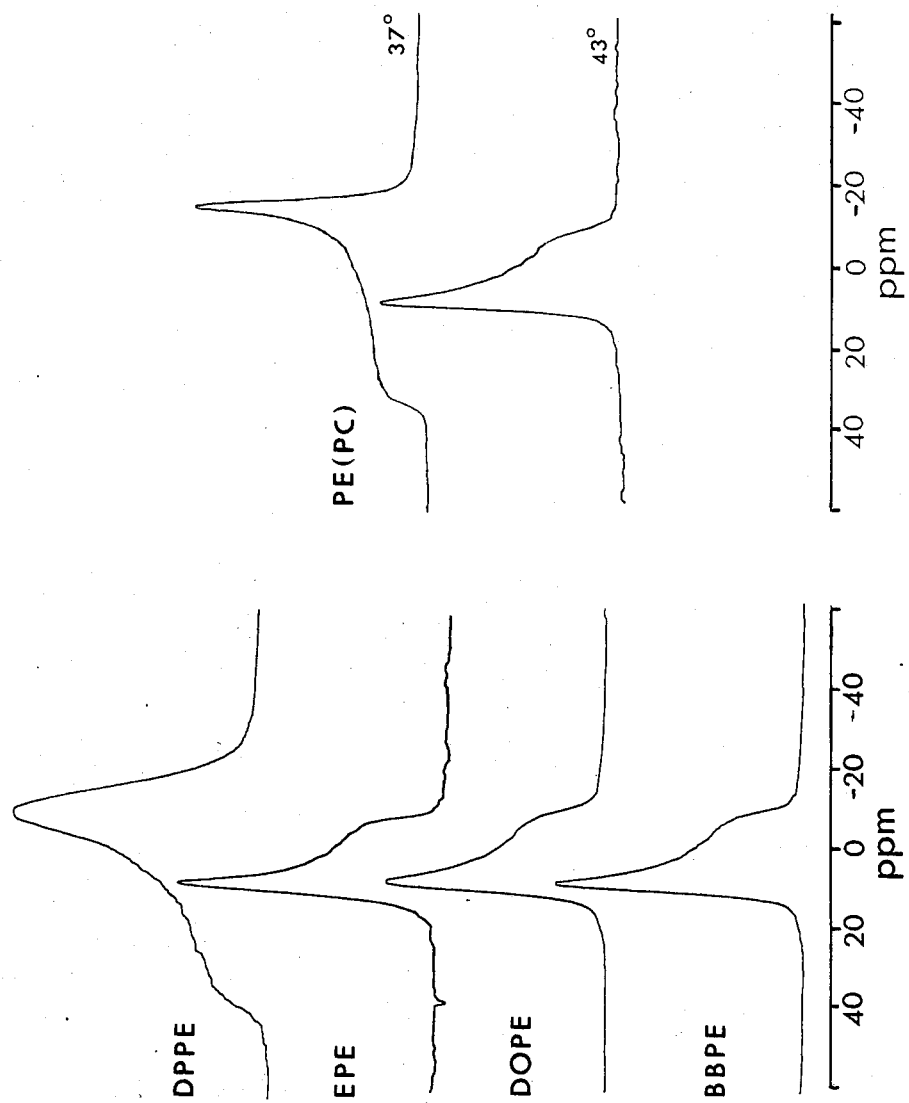
FIG. 1A shows $^{31}P$ NMR of DPPE, DOPE, bovine brain PE (BBPEA), and egg PE (EPE) at 37° C. As shown by these tracings, DOPE, bovine brain PE, and egg PE have a hexagonal organization at 37° C., while DPPE has a lamellar organization at this temperature. These organizations do not change between 37° C. and 43° C.
FIG. 1B shows the $^{31}P$ NMR of egg PE(PC) at 37° C. and 43° C. As shown by these tracings, the structural organization of egg PE(PC) at 37° C. is lamellar, while at 43° C. it is hexagonal.

Of the various macromolecular organizations which have been observed, four are of importance to the present invention, namely, lamellar (bilayer), hexagonal, lipidic particle and perturbed bilayer. As discussed above and as demonstrated in detail below, in accordance with the invention, it has been surprisingly found that only three of these organizations, i.e., the hexagonal, lipidic particle, and perturbed bilayer organizations, can be used to eliminate false postives in lipid-dependent diagnostic assays caused by anti-phospholipid antibodies, while the fourth organization (lamellar) completely fails at this task. While the structures and characteristics of bilayer lipids, hexagonal phase lipids and lipidic particles are well known to those in the art, perturbed bilayer structures are defined here as bilayer-forming rather than micelle-forming lysophospholipids, which exhibit dramatically different chemical shift antisotropy (CSA) as measured by $^{31}$P-NMR than other bilayer phase phospholipids. As a result, these structures might present a surface comparable to the monolayer of phospholipid surrounding hexagonal structures. For example, the CSA of MOPE, a perturbed bilayer lysophosphlipid is $-12$ ppm above 20° C., (FIG. 4) as compared to $-30$ ppm of DPPE which is lamellar, and $-15$ ppm of DOPE, which is hexagonal (FIG. 1). Examples of bilayer-forming lysophospholipids are MOPE, lysolinoleoyl PE and lysolinolenoyl PE, while micelle forming lysophospholipids include monomyristoyl PE (MMPE) and monopalmitoyl PE (MPPE). It is believed that prior art workers were unable to solve the false positive problem because they had not discovered this structural difference.

With this difference in hand, solution of the false positive problem simply involves adding one step to the regular assay protocol, namely, a pre-incubation step wherein the sample to be assayed is incubated with a phospholipid or a mixture of phospholipids know to have a hexagonal organization, a perturbed bilayer organization, or with lipidic particles. As demonstrated below in Example 2, it has been found that this pre-incubation step neutralizes the effects of anti-phospholipid antibodies in the sample being assayed without substantially changing the overall character of the assay, and, in particular, without changing the baseline of the assay for normal samples.

The lipid concentration used and the duration of the incubation will depend on the particular lipid or lipids used, the temperature of incubation, and the particular assay being performed. As illustrated below in Example 2, for a partial thromboplastin time (PTT) assay using activated Thrombofax reagent sold by Ortho Diagnostics, INc., (Raritan, N.J.), and for an incubation time of 10 minutes at 37° C., complete inhibition of the false positive effects of a lupus anticoagulant was achieved with a concentration of egg phosphatidylethanolamine (hexagonal at 37° C.) of 5.4 nanomoles/150 microliters. Similar concentration levels and incubation times and temperatures can be readily established for other assays and other lipids and/or lipidic particles by persons skilled in the art.

The pre-incubation procedure of the present invention can be used with any lipid-dependent diagnostic assay which suffers from the problem of false positives in the presence of anti-phospholipid antibodies. Among the assays to which the present invention is applicable are the following: prothrombin times, partial thromboplastin times, Russell viper venom times, Taipan snake venom times, and cardiolipin-dependent tests for syphilis, e.g., the VDRL test.

Various hexagonal phospholipids, lipidic particles, and bilayer-forming lysophospholipids can be used for the pre-incubation step. In general, hexagonal phospholipids are preferred over lipidic particles because it is easier to prepare phospholipid systems which have a hexagonal organization than to prepare systems which include lipidic particles. The most preferred phospholipids are the lysophophospholipids, which possess the perturbed bilayer structure, as these lipids are liposomal and therefore easier to handle than the hexagonal phospholipids which precipitate.

Examples of lipid systems which include lipidic particles and thus are suitable for use with the present invention include various mixtures of phospholipids which prefer a bilayer organization with phospholipids which prefer a hexagonal organization. Examples of such mistures include: DOPE:DOPC (2:1), and DOPC:cardiolipin:cholesterol:DPPC:alpha-tocophorol (3.0:4.0:1.9:1.0:0.1)).

Examples of suitable hexagonal phase lipids which can be used with the present invention include cardiolipin, phosphatidic acid, and various phosphatidylethanolamines, including egg phosphatidylethanolamine (egg PE), dioleoylphosphatidylethanolamine (DOPE), bovine phosphatidylethanolamine (bovine PE), and egg phosphatidylethanolamine derived from phosphatidylcholine (egg PE(PC)) if used above its lamellar to hexagonal transition temperature, e.g., if used at 43° C., but not at 37° C.

In assays which include calcium, e.g., coagulation assays, it is preferred to select a phospholipid which exists in the hex II phase independent of calcium concentration. In this way, the lipid will not be prone to change phase during the course of the assay. Examples of such lipids include egg PE, DOPE, and bovine PE, of which egg PE and DOPE are most preferred.

A suitable perturbed bilayer lipid which can be used with the present invention is monooleoylphosphatidylethanolamine (MOPE). This lipid forms liposomes and is easy to prepare and use in the assays. The key to the success of the pre-incubation step when using hexagonal phospholipids or lipidic particles is to make sure that the phospholipid or mixture of phospholipids chosen for the incubation is in the hexagonal state under the conditions (e.g., temperature, pH, ionic strength, etc.) used for the incubation. This determination is most conveniently done by means of a $^{31}$P NMR analysis, although other analysis techniques, e.g., freeze fracture and X-ray, can also be used. It is believed that Exner, et al.,'s difficulties with their phosphatidyl ethanolamine fraction were due, in part, to the fact that they did not determine that their lipids were in a hexagonal state, and also, in part, to the fact that they did not incubate their samples with their phospholipids before performing their assays.

As discussed above, in accordance with another of its aspects, the invention provides an assay for use in diagnosing SLE. In accordance with this aspect, a lipid-dependent assay, e.g., a coagulation test or a cardiolipin-dependent syphilis test, is performed on two samples of the patient's plasma, one of which has been pre-incubated with an hexagonal phospholipid, or a mixture of hexagonal phospholipids, with lipidic particles, or with bilayer-forming lysophospholipids. Since the plasma of lupus patients often includes anti-phospholipid antibodies (e.g., lupus anticoagulants) whose effects, as described above, can be neutralized by hex phase lipids, lipidic particles, or bilayer-forming lysophospholipids, patients suffering from lupus and having these antibodies will in general give a positive result for the non-preincubated assay and a normal result for the preincubated sample. By looking for this combination, patients suffering from lupus can be identified.

The lipid-dependent assays which can be used in connection with this aspect of the invention are the same assays for which the pre-incubation step will reduce the occurrence of false positives. Preferred assays are partial thromboplastin time assays (PTT assays) and the VDRL assay for syphilis, the PTT assays being most preferred. The pre-incubation of one of the patient's two plasma samples is performed using the same procedures and the same lipids/lipidic particles as described above and as illustrated in the examples.

Without intending to limit it in any manner, the present invention will now be further described by the following examples which demonstrate that lipidic particles, hexagonal phospholipids, and bilayer-forming lysophospholipids, but not non-lyso lamellar phospholipids, will neutralize the effects of lupus anticoagulants on a PTT test. The materials and methods common to the various examples were as follows.

MATERIALS AND METHODS

Preparation of Phospholipids

Egg phosphatidylethanolamine (PE), egg phosphatidylcholine (PC), dioleoylphosphatidylethanolamine (DOPE), dipalmitoylphosphatidylethanolamine (DPPE), monooleoylphosphatidylethanolamine (MOPE), monomyristoylphosphatidylethanolamine (MMPE), and monopalmitoylphosphatidylethanolamine (MPPE) were purchased from Avanti Polar Lipids, Birmingham, Alabama. Egg PE(PC) was derived from its respective phosphatidylcholine purchased from Sigma Chemical Co. (St. Louis, MO), employing the base exchange capacity of phospholipase D (see Comfurius, P. and Zwall, R. F. A. (1977) *Biochim. Biophys. Acta.* 488, 36–42 and was purified following the procedures described in Tilcock, C. P. S. and Cullis, P. R. (1982) *Biochim. Biophys. Acta.* 684, 212–218. Bovine brain PE was from Supelco (Bellefonte, PA).

Stock solutions were prepared as follows: a volume containing four milligrams of phospholipid in chloroform was placed in a round bottom glass tube and the chloroform removed by evaporation with dry nitrogen. The dried lipids were resuspended in 1.0 ml of 20 mM Hepes buffer (150 mM NaCl, pH 7.5), hydrated at a temperature above their transition temperature for 1–2 hours, and stored at 4° C.

The phosphate concentrations of the phospholipid preparations were determined by the method of Bartlett. See G. R. Bartlett, *J. Biol. Chem.*, Vol. 234, pages 466–468 (1959).

NMR $^{31}$P NMR spectra were obtained using a Bruker WP-200 FT-NMR spectrometer operating at 81.0 MHz for $^{31}$P. Lipids were dispersed in 10 mM Tris/HCl, 100 mM NaCl, 10% v/v $^2$H$_2$O pH 7 buffer by extensive vortexing at room temperature except for DPPE which was heated to 70° C. before dispersal. Spectra were accumulated at 37° C. for up to 2000 transients employing a 7 microsecond 90° r.f. pulse, 20 kHz sweepwidth and 0.8 second interpulse delay, in the presence of broadband proton decoupling. An exponential multiplication corresponding to 50 Hz line-broadening was applied to the spectra prior to Fourier-transformation.

EXAMPLE 1

Production of Lupus Anticoagulants

Using the following procedures, lupus anticoagulants were obtained from hybridomas formed by fusing peripheral blood lymphocytes obtained from patients having SLE with the human lymphoblastoid cell line GM 4672.

Fifty milliliters of venous blood were obtained from 13 patients who satisfied the revised American Rheumatism Association criteria for the classification of SLE. See E. M. Tan, et al., (1982) *Arthritis Rheum.* 25, 1271–1277. The plasma of two of these patients had elevated partial thromboplastin times, and another patient was VDRL positive.

Peripheral blood lymphocytes in these samples were isolated on a Ficoll-Hypaque density gradient and were then fused with the human lymphoblastoid cell line GM 4672, obtained from the Cell Repository Institute of Medical Research, Camden, N.J., at a cell ratio of 1:1, using 44.4% polyethylene glycol. The procedures used for fusion, plating and cloning are described in H. Massicotte, et al., (1984) *Hybridoma* 3(3), 215–222. The antibodies produced by these hybridomas were all IgM immunoglobulins as determined by a solid phase radioimmunoassay (see J. Rauch, et al., (1985) *J. Immunol.* 134, 180–186).

Forty-three (43) hybridoma supernatants were tested for the presence of lupus anticoagulants. Of these 43, 11 were found to exhibit lupus anticoagulant activity, i.e., false positives, in a PTT assay (hereinafter referred to as hybridoma anticoagulants 600, 824, 801, 1105, 1403, 1420, 1401, 1104, 1410, 1109, and 4003). The selection of these hybridomas was performed as follows.

The screening test for the hybridoma antibodies was a modified activated partial thromboplastin time (PTT) assay. See Langdell, R. D. (1971) in *Thrombosis and Bleeding Disorders*, eds. N. U. Bang et al., (Academic Press, New York). This assay (modified as indicated) was also used in Examples 2 and 3 below to identify phospholipids and lipidic particles capable of inhibiting the effects of the lupus anticoagulants.

The screening test was performed as follows. Fifty ul of hybridoma culture supernatant were diluted with an equal volume of freshly reconstituted pooled normal human plasma sold under the trademark Verify Normal Citrate (General Diagnostics, Scarborough, Ontario) in a 13×100 mm borosilicate glass tube.

One hundred ul of a 1/64 dilution of activated Thrombofax (Ortho Diagnostics Inc., Raritan, N.J.) in Hepes buffer, which had been prewarmed to 37° C., were then added and incubated for 5 minutes in a 37° C. circulating water bath (Haake, Saddle Brook, N.J.). The 1/64 dilution was found to significantly increase the sensitivity of the assay to anti-phospholipid antibodies. Higher and lower dilutions were found not to work as well.

Next, one hundred ul of a 2 mg/ml solution of kaolin (Fisher Scientific, Fair Lawn, N.J.) in 0.1M Tris-HCl buffer, pH 7.6, were added and incubated for 5 minutes in the 37° C. water bath, with shaking at 2-minute intervals.

Finally, one hundred ul of 0.025M CaCl$_2$ were added to the mixture and a stopwatch was started. The tilt-tube technique was used in which the tube was gently tilted back and forth in the 37° C. water bath until a clot formed. The stopwatch was stopped at the first sign of a clot and the time recorded. All samples were tested in duplicate. Controls in each assay included the culture supernatant of the GM 4672 parent cell line (IgG-producing) and of clone 1500, a PTT-negative hybridoma (IgM-producing).

The 11 lupus anticoagulant-producing hybridomas were selected using the following criteria. The supernatant produced by GM 4672, the parent lymphoblastoid cell for all of the hybridomas, was used as a negative control. This supernatant contains GM 4672 IgG and has no lupus anticoagulant activity relative to Verify normal plasma (PTT ratio 1.00/1.00). The clotting times of the test supernatants from the 43 hybridoma clones, which contained varying immunoglobulin concentrations between 0.03 and 74.0 ug/ml, were compared to this control. An antibody was defined as having anticoagulant activity if its PTT exceeded the PTT of the GM 4672 control by more than 6 seconds (0.1 minutes).

Of the forty-three clones, twenty-three gave PTT values below or equal to that of the GM 4672 control. Another 9 antibodies never exceeded the control by more than 0.02 minutes, with a mean ± standard deviation of 0.012 min ± 0.004. Since in plasma studies, the mean +2 standard deviations has been accepted as representing the upper limit of normality, these nine were considered as not meeting the selection criterion. See Barrowcliffe, T. W. and Gray, E. (1981) *Thromb. Hawmostat.* 46, 629-637. The remaining 11 had clotting times more than 6 seconds greater than the control and were used in the subsequent experiments.

EXAMPLE 2

Inhibition of Lupus Anticoagulants by Hexagonal Phase Phospholipids

The effects of different phospholipids systems on the partial thromboplastin times of the 11 human hybridoma lupus anticoagulants identified in Example 1 were assessed using the following procedures.

Seventy-five ul of hybridoma culture supernatant was mixed with an equal volume of the phospholipid being tested, and the mixture was incubated for 10 minutes in a 37° C. water bath. Fifty microliters of this mixture was then added to 50 ul of Verify Normal Citrate, in duplicate, and the rest of the PTT assay was performed exactly as described above in Example 1. Controls in each assay included GM 4672 supernatant diluted 1:1 with phospholipid, and each hybridoma supernatant diluted 1:1 with Hepes buffer, which was taken to represent 100% activity for that supernatant.

Statistical analysis of the difference between PTT ratio values (sample/control) in the absence and presence of different phospholipid systems was performed using the sign test. See Siegel, S. (1956) *Nonparametric Statistics for the Behavioral Sciences* (McGraw-Hill, New York). Comparisons were always made with buffer (no phospholipid) controls run in the same experiment.

The configurations of the phospholipids tested (Bovine PE, Egg PE, DOPE, DPPE, and Egg PE(PC)) were determined using the $^{31}P$ NMR procedure described above at both 37° C. and 43° C. Representative tracings are shown in FIGS. 1A and 1B. As shown in FIG. 1A, DOPE, bovine brain PE, and egg PE have a hexagonal II organization at 37° C., while DPPE has a lamellar (gel) organization at this temperature. These organizations do not change between 37° C. and 43° C. As shown in FIG. 1B, the structural organization of egg PE(PC) at 37° C. is lamellar (liquid crystalline), while at 43° C. it is hexagonal II.

The results of the tests are shown in Table I, where the PTT values are given as ratios of the PTT (expressed in minutes) of the hybridoma anticoagulants pre-incubated with the various phospholipids over the PTT of the same hybridoma anticoagulants pre-incubated with buffer. As shown in that table, hybridoma lupus anticoagulants incubated with buffer had PTT values ranging between 1.10 and 1.20 minutes. This represented a prolongation of 0.10 to 0.20 minutes (6-12 seconds) over the negative GM 4672 and hybridoma 1500 controls (PTT values between 0.98 and 1.04 minutes). No correlation was observed between the extent of elongation and immunoglobulin concentration, which, as indicated above, ranged from 0.03 to 74.0 ug/ml.

With regard to the present invention, Table I clearly shows that the hexagonal lipids inhibited the lupus anticoagulants, while the lamellar lipids did not. Moreover, the hexagonal lipids did not change the baseline of the assay as can be seen from the fact that the GM 4672 and hybridoma 1500 controls gave essentially the same PTT values with and without the hexagonal phospholipids.

More specifically, Table I shows that bovine and egg PE (which are hexagonal phospholipids at 37° C.) produced PTT values equivalent to the GM 4672 and 1500 controls for all 11 antibodies, demonstrating complete inhibition of lupus anticoagulant activity (p less than 0.0005). Similarly, DOPE (hexagonal at 37° C.) also completely inhibited the activity of all 11 hybridoma anticoagulants (p less than 0.0005). Five of the 11 antibodies were inhibited by 2.7 nanomoles of DOPE ($\frac{1}{2}$ the amount of bovine PE added), while the other 6 required higher amounts of DOPE (6.75-67.5 nanomoles phosphorus) for complete inhibition.

In contrast to the results achieved with these hexagonal lipids, DPPE and egg PE(PC) (both lamellar at 37° C.) caused no statistically significant inhibition at concentrations 1.5 to 48 fold greater than that of DOPE.

Figure 2:
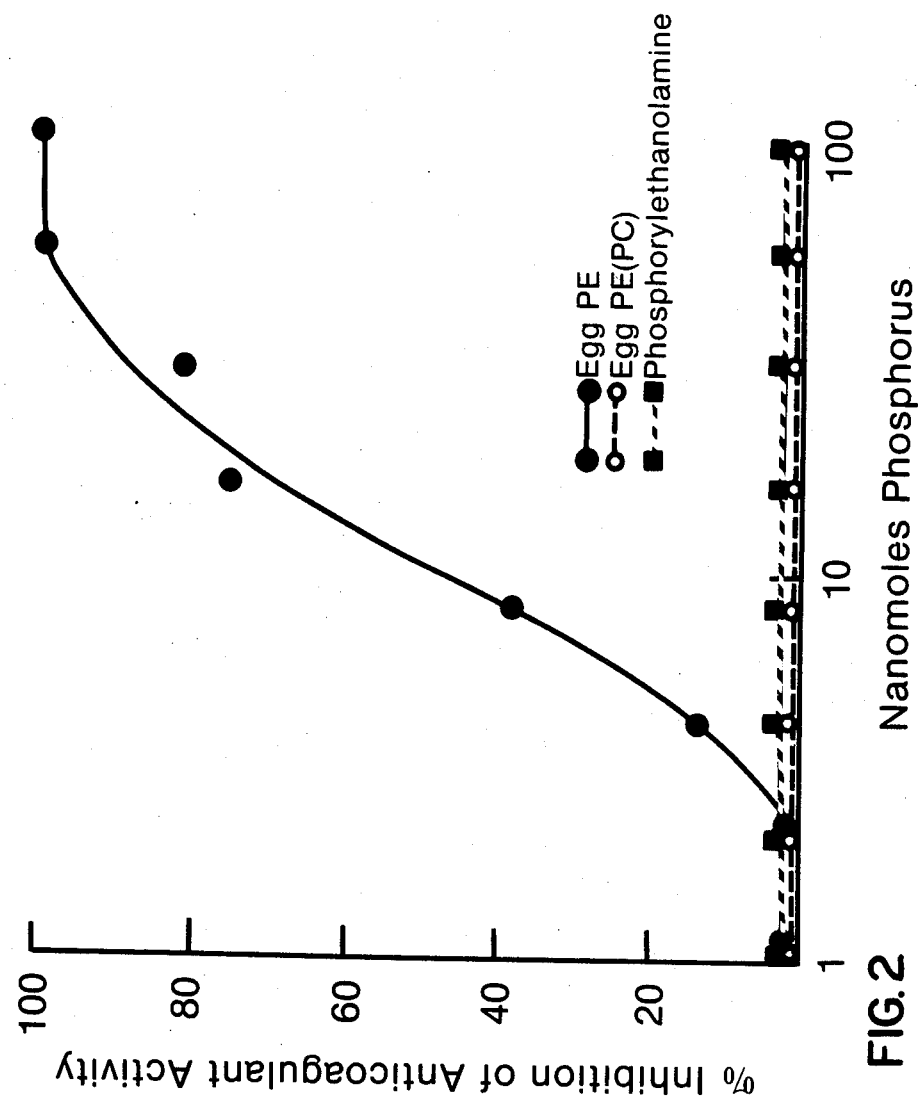
FIG. 2 shows titration of the inhibition of the anticoagulant activity of antibody 824 after pre-incubation with egg PE, egg PE(PC), or phosphorylethanolamine at 37° C. At this temperature, egg PE is hexagonal and egg PE(PC) is lamellar. Hybridoma lupus anticoagulant 824 was pre-incubated for 10 minutes at 37° C. with Hepes buffer, egg PE, egg PE(PC), or phosphorylethanolamine. This mixture was then tested, in duplicate, for lupus anticoagulant activity. The percent of inhibition of anticoagulant activity was calculated by defining the PTT of the anticoagulant 824+buffer (1.18 min.) as maximum anticoagulant activity and the mean PTT of the negative controls, GM 4672 IgG and 1500 IgM (1.02 min.), as minimum anticoagulant activity. The percent inhibition was calculated using the formula.

The effects of different concentrations of phospholipid on the inhibitory level achieved is shown in FIG. 2. The data presented in this figure was obtained as follows.

Dilutions of egg PE, egg PE(PC), and phosphorylethanolamine, the polar head group of PE, containing between 1.04 to 133.75 nanomoles phosphorus, were added to hybridoma lupus anticoagulant 824 and pre-incubated for 10 minutes at 37° C. This anticoagulant had the lowest immunoglobulin concentration of all of the hybridoma anticoagulants, but nonetheless, had good PTT activity.

Positive controls comprised anticoagulant 824 incubated with Hepes buffer. Negative controls comprised GM 4672 or hybridoma 1500 IgM incubated with buffer, egg PE, egg PE(PC), or phosphorylethanolamine.

Fifty microliters of these mixtures were tested, in duplicate, in the PTT assay of Example 1. Maximum anticoagulant activity of anticoagulant 824 (0% inhibition) was defined as the PTT value of 824+buffer (1.18 minutes), while minimum anticoagulant activity was defined as the mean PTT value of the negative controls (1.02 minutes ±0.02) % inhibition was calculated using the formula:

$$\% \text{ inhibition} = \frac{PTT \text{ (maximum)} - PTT \text{ (sample)}}{PTT \text{ (maximum)} - PTT \text{ (minimum)}} \times 100\%$$

As shown in FIG. 2, inhibition of the anticoagulant activity by egg PE, which is hexagonal at 37° C., occurred when greater than 2.1 nanomoles phosphorus were added and was complete at 68 nanomoles phosphorus. On the other hand, egg PE(PC), which is lamellar (liquid crystalline) at 37° C., and phosphorylethanolamine, the polar head group of PE, failed to inhibit anticoagulant activity over the same range of concentrations.

As a further demonstration that it is the configuration of the lipid which is important, the 11 anticoagulants were pre-incubated with egg PE(PC) at 37° C. and 43° C., where egg PE(PC) is lamellar and hexagonal, respectively. The results are shown in FIG. 3, along with the results obtained by pre-incubation of the anticoagulants with egg PE at 43° C. (hexagonal).

More particularly, the data in FIG. 3 was obtained as follows. Egg PE(PC) and egg PE were hydrated in Hepes buffer at 37° C. and aliquots were heated at 43° C. for 1 hour. The pre-incubation of the phospholipids or buffer with the lupus anticoagulants or controls was performed as described above in this example, except that the incubation was done at 43° C. Control tubes in which the lupus anticoagulant was pre-incubated with the same phospholipids or buffer at 37° C. were included in each experiment.

In order to prevent the phospholipid configuration in the 43° C. pre-incubation mixture from being altered by exposure to the 37° C. incubation temperature of the PTT assay, the phospholipid in the 43° C. preincubation mixture was removed by filtration through a 13 cm, 0.22 micron Millipore filter unit, which had been preheated to 45° C. The filtrates were then assayed using the PTT assay protocol described above in this example. Lupus anticoagulants, preincubated with the same phospholipids at 37° C. and then filtered through un-heated, 13 mm, 0.22 micron filter units served as controls.

As shown in FIG. 3, heating of the egg PE(PC) completely changed its ability to inhibit the anticoagulants. At 37° C., egg PE(PC) is lamellar, and as shown in FIG. 3, is incapable of inhibiting lupus anticoagulant activity. At 43° C., however, egg PE(PC) assumes a hexagonal configuration (see FIG. 1). As shown in FIG. 3, in this arrangement, egg PE(PC) dramatically inhibits the anticoagulant activity of the same lupus anticoagulants.

Significantly, as also shown in FIG. 3, the lupus anticoagulants when heated to 43° C. in the presence of buffer retained all of their anticoagulant activities. Also, egg PE when heated continues to inhibit the lupus anticoagulants, although to a somewhat smaller extent.

In summary, this example clearly demonstrates that hexagonal phospholipids will inhibit lupus anticoagulants and thus eliminate the problem of false positives in a PTT assay, while lamellar phospholipids cannot do so.

EXAMPLE 3

Inhibition of Lupus Anticoagulants By Lipidic Particles

This example demonstrates that lipidic particles will inhibit the effects of lupus anticoagulants.

A DOPC:DOPE (1:2) solution was prepared following the procedures described above and having a lipid concentration of 4 mg/ml (DOPE equivalents). Shortly after its preparation, this solution was pre-incubated with the supernatant from hybridoma 824 for 10 minutes at 37° C. No inhibitory effect was observed at that time, the PTT ratio being 1.12/1.00 (GM 4672 supernatant as the control).

The solution was then stored for 5 days. As is known in the art, DOPC:DOPE mixtures are unstable and will form lipidic particles upon storage. After the five day storage period, the solution was again tested for its ability to inhibit lupus anticoagulants. The PTT ratio measured at this point in time was 1.06/1.06 demonstrating that complete inhibition had been achieved. A parallel experiment with a DPPC:DOPE (1:2) mixture showed no change over time (the mixture would not inhibit the anticoagulant either before or after storage), which is consistent with the fact that this mixture is not known to generate lipidic particles during storage.

EXAMPLE 4

Inhibition of Lupus Anticoagulants by Lysophospholipid

Monooleoylphosphatidylethanolamine may be expressed as

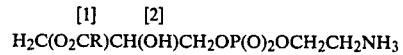

$$H_2C(O_2CR)CH(OH)CH_2OP(O)_2OCH_2CH_2NH_3$$

wherein R is the oleoyl group attached to the carbon in the 1-position, as labeled [1], thus 1-oleoyl. The (OH) group is located on the [2] carbon. This lipid may be further expressed as sn-1-18:$1_{cis}$-PE, denoting the 18 carbon composition of the oleoyl group, followed by a number denoting the number of double bonds, in this case 1 double bond in the cis configuration. As a further illustration of the nomenclature, for example, more highly unsaturated bilayer-forming LPE's, wherein R is in the 1-position and has 2 or 3 double bonds and 17 carbon atoms; are expressed as lysolinolenoyl PE or sn-1-18:$2_{cis}$-PE and lysolinolenoyl PE or sn-1-18:$3_{cis}$-PE, respectively. The carboxylate carbon atom is the 18th carbon atom.

Alternatively, the micelle-forming lysophospholipids monomyristoylphosphatidylethanolamine (MMPE) and monopalmitoylphosphatidylethanolamine (MPPE) are expressed similarly to the above MOPE, but have 14 and 16 carbon atoms, respectively, instead of the 18 carbon atoms of MOPE. MMPE and MPPE may be expressed as sn-1-14:0 PE and sn-1-16:0 PE, respectively; each lipid being fully saturated.

This example demonstrates that a perturbed bilayer lysophospholipid, MOPE, will inhibit the effects of lupus anticoagulants.

Solutions of MOPE, MMPE and MPPE were prepared following the procedures described above, at a lipid concentration of 4 mg/ml. The effects of these lysophospholipids on the partial thromboplastin times of 2 of the human hybridoma lupus anticoagulants, 824 and 1105, and control 1500 were assessed using the following procedures.

The hybridoma lupus anticoagulants or control antibody 1500 were mixed with an equal volume of a lyso PE, or buffer as described in Example 2. All samples were tested in duplicate.

The results of the tests are shown in Table II, where PTT values are given for preincubation of lupus anticoagulant antibodies and the control antibody, with 3 different lysophosphatidylethanolamines. PTT clotting times for each of the samples are given in seconds. As shown in Table II, hybridoma lupus anticoagulants incubated with buffer had PTT values of 71 seconds. This represented a prolongation of 0.12 minutes (7 seconds) over the hybridoma 1500 control (PTT value of 64 seconds).

With regard to the present invention, Table II clearly shows that MOPE inhibited the lupus anticoagulants, giving a PTT value at the control level; while MMPE and MPPE showed no inhibition. Moreover, the MOPE did not change the baseline of the assay, as the hybridoma 1500 control gave essentially the same PTT value with or without MOPE. In contrast, results achieved with MMPE and MPPE caused no statistically significant inhibition.

EXAMPLE 5

Diagnosis for Lupus—Correction of False Positives for a Plasma Sample

This example illustrates the use of the present invention as a tool for diagnosing systemic lupus erythematosus (SLE).

Following standard procedures, two plasma samples were obtained from a patient having symptoms characteristic of SLE. One of the samples was incubated for 10 minutes at 37° C. with DOPE at a concentration of 6.75 nanomoles/150 microliters. The other sample was incubated with buffer at the same temperature and for the same time period.

Thereafter, the PTT assay of Example 1 was performed on each of the samples. The sample incubated with DOPE gave a normal reading, while the sample incubated with buffer gave a positive reading.

These results in combination with other test results, including the patient's presenting symptoms, indicated that the patient was, in fact, suffering from SLE. These results also show that the presence of false positives for a PTT assay performed on the plasma of a patient who produces lupus anticoagulants can be corrected by the procedures of the present invention.

TABLE 2

Preincubation of Lysophosphatidylethanolamines with Hybridoma Lupus Anticoagulants at 37° C.: Effects on Partial Thromboplastin Times Clotting Time (sec) of Hybridoma Antibody after Preincubation with:

| Hybridoma Antibody | Buffer | Monooleoyl PE | Monomyristoyl PE | Monopalmitoyl PE |
|---|---|---|---|---|
| Control 1500 | 64[a] | 63 | 64 | 64 |
| 824 | 71 | 63 | 71 | 71 |
| 1105 | 71 | 63 | 70 | 71 |

[a]Each value represents the mean of duplicate samples in the PTT assay. Hybridoma antibodies, including the 1500 control hybridoma IgM antibody with no anticoagulant activity, were preincubated with a 0.12 mg/ml solution of monooleoyl PE, monomyristoyl PE, or monopalmitoyl PE for 10 minutes at 37° C. and then tested in the routine PTT assay. Incubation of the hybridoma anticoagulants 824 and 1105 with monooleoyl PE resulted in PTT values equivalent to the PTT of the IgM control (i.e. completely inhibited anticoagulant activity). In contrast, preincubation of the hybridoma anticoagulants 824 and 1105 with monomyristoyl PE and monopalmitoyl PE resulted in PTT values equivalent to the PTT values of the antibodies plus buffer, demonstrating that these phospholipids did not inhibit lupus anticoagulant activity.

What is claimed is:

1. In a lipid-dependent diagnostic assay which is performed on a test sample and which is subject to false positives if the test sample includes anti-phospholipid antibodies, the improvement comprising pre-incubating the test sample with a bilayer-forming lysophospholipid.

2. The assay of claim 1 wherein the lysophospholipid is monooleoylphosphatidylethanolamine.

3. The assay of claim 1 wherein the lysophospholipid is lysolinoleoylphosphatidylethanolamine or lysolinolenoylphosphatidylethanolamine.

4. The assay of claim 1 wherein the test sample is human plasma and the assay is a coagulation test.

5. The assay of claim 4 wherein the assay is a partial thromboplastin time assay.

6. The assay of claim 1 wherein the test sample is human plasma and the assay is a syphilis test.

TABLE 1

Effects of Preincubation of Different Phospholipid Phase Systems with Lupus Anticoagulants at 37° C.

PTT (minutes) (Antibody + Phospholipid/Antibody + Buffer)[a] Phospholipid System Incubated with Lupus Anticoagulant[b]

| Hybridoma Number | IgM (ug/ml) | Bovine PE (Hexagonal) (5.4 nmoles) | Egg PE (Hexagonal) (5.4 nmoles) | DOPE (Hexagonal) (2.7 nmoles) | DPPE (Lamellar) (131 nmoles) | Egg PE(PC) (Lamellar) (100 nmoles) |
|---|---|---|---|---|---|---|
| Controls[c] | | | | | | |
| GM 4672 IgG | 0 | 1.00/1.00 | 0.99/1.00 | 1.03/1.04 | 1.02/1.02 | 0.98/0.98 |
| 1500 IgM | 12.0 | 1.00/1.00 | 1.00/1.00 | 1.04/1.04 | 1.02/1.02 | 0.98/0.98 |
| Anticoagulants | | | | | | |
| 600 | 0.7 | 0.99/1.14 | 1.00/1.14 | 1.04/1.16 | 1.14/1.14 | 1.16/1.16 |
| 824 | 0.03 | 1.00/1.14 | 1.00/1.16 | 1.04/1.14 | 1.14/1.14 | 1.12/1.12 |
| 801 | 16.0 | 1.00/1.12 | 1.00/1.12 | 1.00/1.16[f] | 1.12/1.12 | 1.09/1.08 |
| 1105 | 9.5 | 1.00/1.12 | 1.00/1.12 | 1.05/1.19 | 1.16/1.17 | 1.15/1.14 |
| 1403 | 23.0 | 1.00/1.14 | 1.00/1.14 | 1.02/1.13[e] | 1.14/1.14 | 1.15/1.16 |
| 1420 | 9.2 | 1.00/1.10 | 1.00/1.10 | 1.03/1.13 | 1.10/1.11 | 1.16/1.16 |
| 1401 | 30.0 | 1.00/1.14 | 1.00/1.14 | 1.02/1.13[f] | 1.20/1.20 | 1.18/1.20 |
| 1104 | 9.0 | 1.00/1.14 | 1.00/1.14 | 1.00/1.14 | 1.15/1.14 | 1.14/1.15 |
| 1410 | 2.5 | 1.00/1.12 | 1.00/1.12 | 1.02/1.12[e] | 1.12/1.12 | 1.14/1.14 |
| 1109 | 74.0 | 1.00/1.10[d] | 1.00/1.10[d] | 1.03/1.14[e] | 1.14/1.14 | 1.14/1.15 |
| 4003 | 0.22 | 0.99/1.18 | 1.00/1.18 | 0.98/1.18[f] | 1.14/1.15 | 1.18/1.18 |

[a]All PTT values are shown as ratios of the PTT for antibody incubated with phospholipid over the PTT of antibody incubated with buffer.
[b]PTT values in the presence of phospholipid were compared to buffer controls. Differences were highly significant (p less than 0.0005) for bovine PE, egg PE, and DOPE, but not statistically significant for DPPE and egg PE(PC).
[c]Negative controls included an IgG myeloma antibody (GM 4672) and an IgM hybridoma antibody (1500), which had PTT values equivalent to Verify normal plasma plus buffer (varying from 0.98-1.04 min., depending on the particular assay.)
[d]Required 13.5 nanomoles for complete inhibition.
[e]Required 6.75 nanomoles for complete inhibition.
[f]Required 67.5 nanomoles for complete inhibition.

7. The assay of claim 6 wherein the assay is a cardiolipin-dependent syphilis test.

8. An assay for use in determining whether a patient has systemic lupus erythematosus comprising the steps of:
   (a) obtaining first and second samples of the patient's plasma;
   (b) incubating the first sample with bilayer-forming lysophospholipid;
   (c) performing a lipid-dependent diagnostic assay on both the first and second samples, the assay producing a positive reading when used to assay a sample which contains anti-phospholipid antibodies;
   (d) comparing the results of the assays performed on the first and second samples, the presence of a normal result for the first sample and a positive result for the second sample being indicative of the patient having systemic lupus erythematosus.

9. The assay of claim 8 wherein the lysophospholipid is monooleoylphosphatidylethanolamine.

10. The assay of claim 8 wherein the lysophospholipid is lysolinoleoylphosphatidylethanolamine or lysolinolenoylphosphatidylethanolamine.

11. The assay of claim 8 wherein the lipid-dependent assay is a coagulation test.

12. The assay of claim 11 wherein the lipid-dependent assay is a partial thromboplastin time assay.

13. The assay of claim 8 wherein the lipid-dependent assay is a syphilis test.

14. The assay of claim 13 wherein the lipid-dependent assay is a cardiolipin-dependent syphilis test.

* * * * *